(12) United States Patent
Lacot et al.

(10) Patent No.: US 6,476,916 B1
(45) Date of Patent: Nov. 5, 2002

(54) ACTIVE OPTICAL DETECTOR

(75) Inventors: Eric Lacot, St Martin d'Heres; Frederic Stoeckel, Uriage, both of (FR)

(73) Assignee: Universite Joseph Fourier, Grenoble/Cedex (FR)

( * ) Notice: Subject to any disclaimer, the term of this patent is extended or adjusted under 35 U.S.C. 154(b) by 0 days.

(21) Appl. No.: 09/509,758

(22) PCT Filed: Sep. 30, 1998

(86) PCT No.: PCT/FR98/02092

§ 371 (c)(1),
(2), (4) Date: Jun. 21, 2000

(87) PCT Pub. No.: WO99/17099

PCT Pub. Date: Apr. 8, 1999

(30) Foreign Application Priority Data

Sep. 30, 1997 (FR) .............................. 97 12391

(51) Int. Cl.⁷ .............................. G01N 21/55; A01S 3/10
(52) U.S. Cl. .............................. 356/445; 372/26
(58) Field of Search ............. 356/445, 447; 250/201.1, 204, 201.9; 372/36, 28, 38

(56) References Cited

U.S. PATENT DOCUMENTS

| 4,071,751 A | * | 1/1978 | Waksberg | .................. 250/201 |
|---|---|---|---|---|
| 4,243,320 A | | 1/1981 | Gordon | .................... 356/73.1 |
| 5,272,708 A | | 12/1993 | Esterowitz et al. | ........... 372/20 |
| 5,546,189 A | * | 8/1996 | Svetkoff et al. | ............. 356/376 |
| 5,757,831 A | * | 5/1998 | Kmetec et al. | ................ 372/38 |
| 6,243,169 B1 | * | 6/2001 | Drabarek et al. | ........... 356/489 |

FOREIGN PATENT DOCUMENTS

DE 28 52 614 A1 6/1979

* cited by examiner

Primary Examiner—Michael P. Stafira
(74) Attorney, Agent, or Firm—Duane Morris LLP

(57) ABSTRACT

Disclosed is a modidied acrylic coating composition cured with melamine characterized by improved inpact resistance which comprises: An acrylic polyol dissolved in a suitable solvent to 40–90% solids; 2 to 50% by weight of said acrylic polyol subatituted with a polytrimethylene carbonate polyol selected from a polytrimethylene carbonate diol, a polytrimethylene carbonate triol, or a higher functionality polytrimethylene carbonate polyol; a melamine crosslinking agent; optionally a catalyst; and optionally pigments and other additives commonly used in coatings. Also disclosed in a related embodiment is a melamine/urea formaldehyde polytrimethylene carbonate coating composition that is prepared without acrylic.

6 Claims, 2 Drawing Sheets ive Optical Detector

ACTIVE OPTICAL DETECTOR

FIELD OF THE INVENTION

The present invention relates to an optical sensor and more specifically to an active optical sensor emitting a light beam in an area to be studied and analyzing the light sent back or transmitted by this area.

SUMMARY OF THE INVENTION

A more specific object of the present invention is to provide such a sensor that operates even when an area of a medium to be studied only sends back or transmits a very small portion of the received light.

Thus, the present invention especially applies to the detection of obstacles or interfaces in diffusing mediums, for example in organic mediums.

The present invention aims at the cases where the reemitted light is difficult to detect by conventional methods using for example chopper and synchronous detection systems.

The present invention provides reinjecting into a laser a light reemitted at a frequency shifted with respect to the laser emission frequency, by using a specific type of laser, that is, a class B laser that, when light is reinjected therein at a frequency shifted by a value substantially corresponding to a natural frequency or relaxation frequency of this laser, generates a modulated laser beam, the modulation amplitude corresponding to a factor on the order of $10^3$ to $10^6$ with respect to a conventional heterodyne detection.

More specifically, the present invention provides an optical sensor including a class B laser source emitting a beam at a first optical frequency; means interacting with the beam to provide a radiation at a modified optical frequency, the shifting between the first frequency and the modified frequency being close to a relaxation frequency of the laser; means for irradiating a selected area of a medium to be studied with the radiation at the modified frequency; means for injecting into the laser light sent back by the selected area; and means for detecting the disturbance brought to the laser emission by the reinjected light.

According to an embodiment of the present invention, the sensor includes means for scanning the area to be studied.

According to an embodiment of the present invention, the sensor includes means of frequency scanning of the radiation emitted by the laser.

According to an embodiment of the present invention, the irradiation means are formed of a lens.

According to an embodiment of the present invention, the detection means include a photodetector followed by a synchronous detection system.

According to an embodiment of the present invention, the means for providing a radiation at a modified optical frequency consist of a medium having an electro-optical or acousto-optical effect excited by an oscillator at a frequency corresponding to the difference between the modified optical frequency and the first optical frequency or one of its submultiples.

The foregoing objects, features and advantages of the present invention will be discussed in detail in the following non-limiting description of specific embodiments in connection with the accompanying drawings.

DETAILED DESCRIPTION OF THE INVENTIONS

Figure 1:
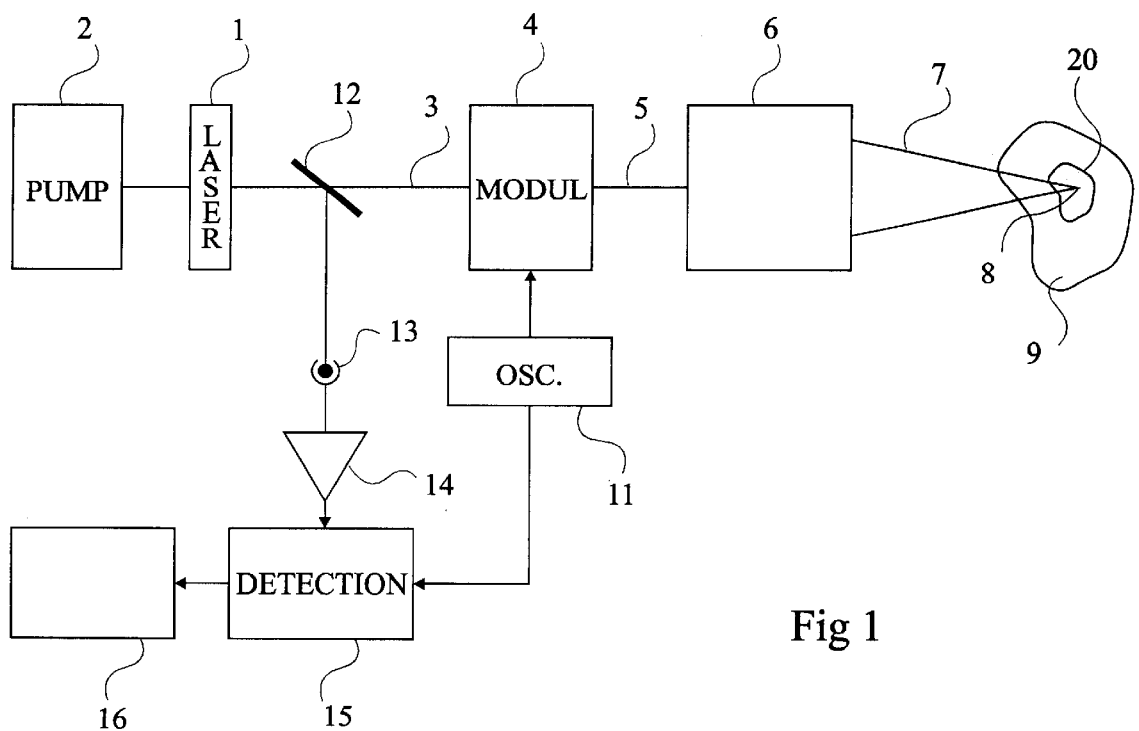
FIG. 1 is a schematic block diagram of a first embodiment of the present invention.

As shown in FIG. 1, the present invention uses an optically or electrically pumped class B laser 1. In the embodiment shown, an optical pumping symbolized by an optical pump 2 is used. Beam 3 emitted by the laser crosses an optical modulator 4, which provides at its output a laser beam 5 including at least a portion of the incident energy, frequency-shifted by a frequency F and/or one or several of its integer multiples. Laser beam 5, with its shifted frequency or frequencies, is sent onto an optical system 6 that provides a redirected beam 7 focused on a point 8 of a medium 9. The return light reemitted by reflection and/or back scattering from the focusing point is transformed back by lens 6 into a beam that returns to laser 1, the operation of which is affected in a way described hereafter.

Modulator 4 is controlled by an oscillator 11 operating at a frequency F. A portion of the beam emitted by the laser is sent by a beam splitter 12 to a photodetector 13, preferably followed by an amplifier 14, the output of which is preferably detected by a synchronous detection signal 15 that enables detecting the signal received at frequency F (and/or at a multiple of this frequency). Synchronous detector 15 is connected to an information supply device 16, for example, a display system.

The operation of the sensor according to the present invention is based as previously indicated on the use of a class B laser. Such a laser, the scientific definition of which is that it is a laser for which the lifetime of the population inversion of the amplifying medium is greater than the lifetime of the laser cavity, may be a semiconductor laser or a solid laser.

The laser may be equipped with one or several optical elements that enable selecting and/or scanning the optical frequency or frequencies. The laser may emit a single optical frequency (monomode laser) or several optical frequencies (multimode laser). The laser emission may be polarized or not. This laser may be pumped by a so-called pump laser if the pumping must be optical. The pumping may also be electric as is generally the case for semiconductor lasers. The optical frequency range emitted by laser 2 is adapted to the optical responses of the mediums to be analyzed or to be detected.

A class B laser has the specificity that, when light is reinjected therein at a modified frequency shifted by a frequency F (or by a multiple of a frequency F) close to a natural frequency or relaxation frequency of the laser, a modulation of the light intensity occurs at frequency F. This amounts to an amplification of the reinjected power by a factor that may, according to the laser and according to the setting of the shifting frequency, be on the order of $10^3$ to $10^6$.

Optical frequency shifter 4 enables generating from a light beam emitted by the laser at an optical frequency, called the carrier frequency, one or several optical beams 5 at one or several frequency-shifted optical frequencies. This frequency shifting occurs at a frequency F and/or at its integer multiples. The frequency shift may be positive and/or negative.

The optical frequency shifting may occur by means of an amplitude modulation or a frequency or phase modulation of the wave emitted by the laser. The amplitude modulation may be performed by means of a modulator having an electro-optical or acousto-optical effect. The frequency or phase modulation may be performed by means of a medium having an electro-optical effect.

One or several of these optical elements may be mobile or enable a deviation or a translation of the optical beam.

The optical system may include one or several optical filters enabling filtering or attenuating the light reinjected into the laser.

Beam splitter 12 has the purpose of sampling a portion of beam 3 sent onto the object to be measured to deviate it towards a photodetector 13. It should be noted that this beam splitter may be selective in optical frequency or in optical polarization.

Figure 2:
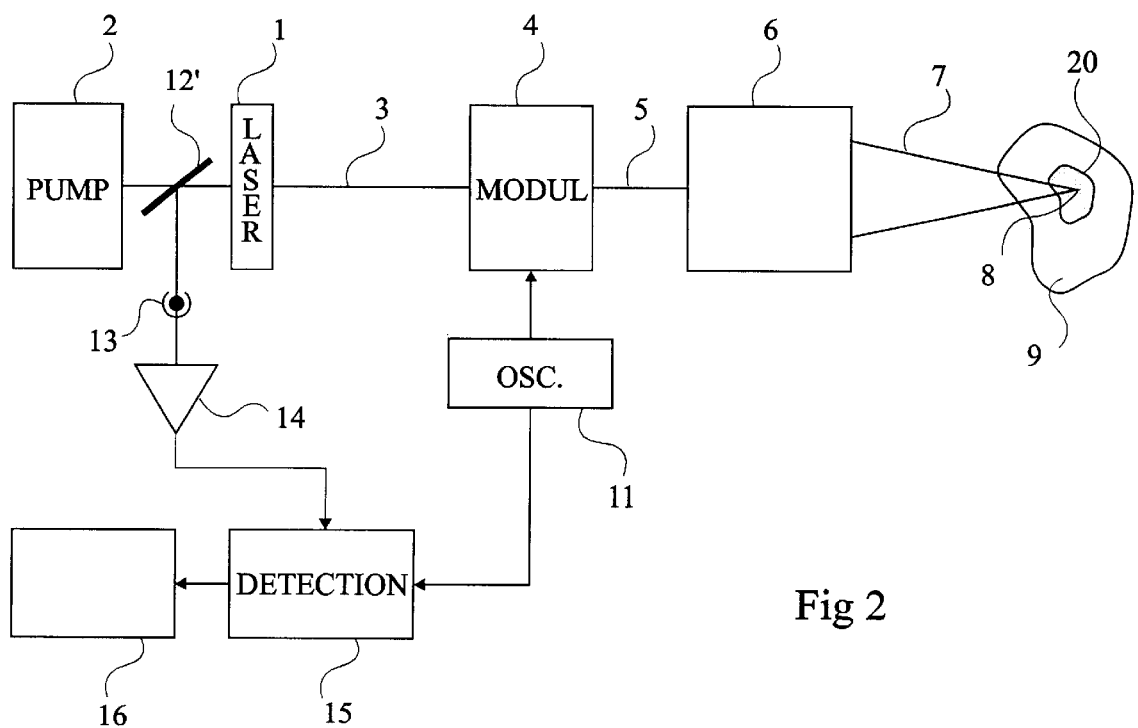
FIG. 2 is a schematic block diagram of a second embodiment of the present invention.
Figure 3:
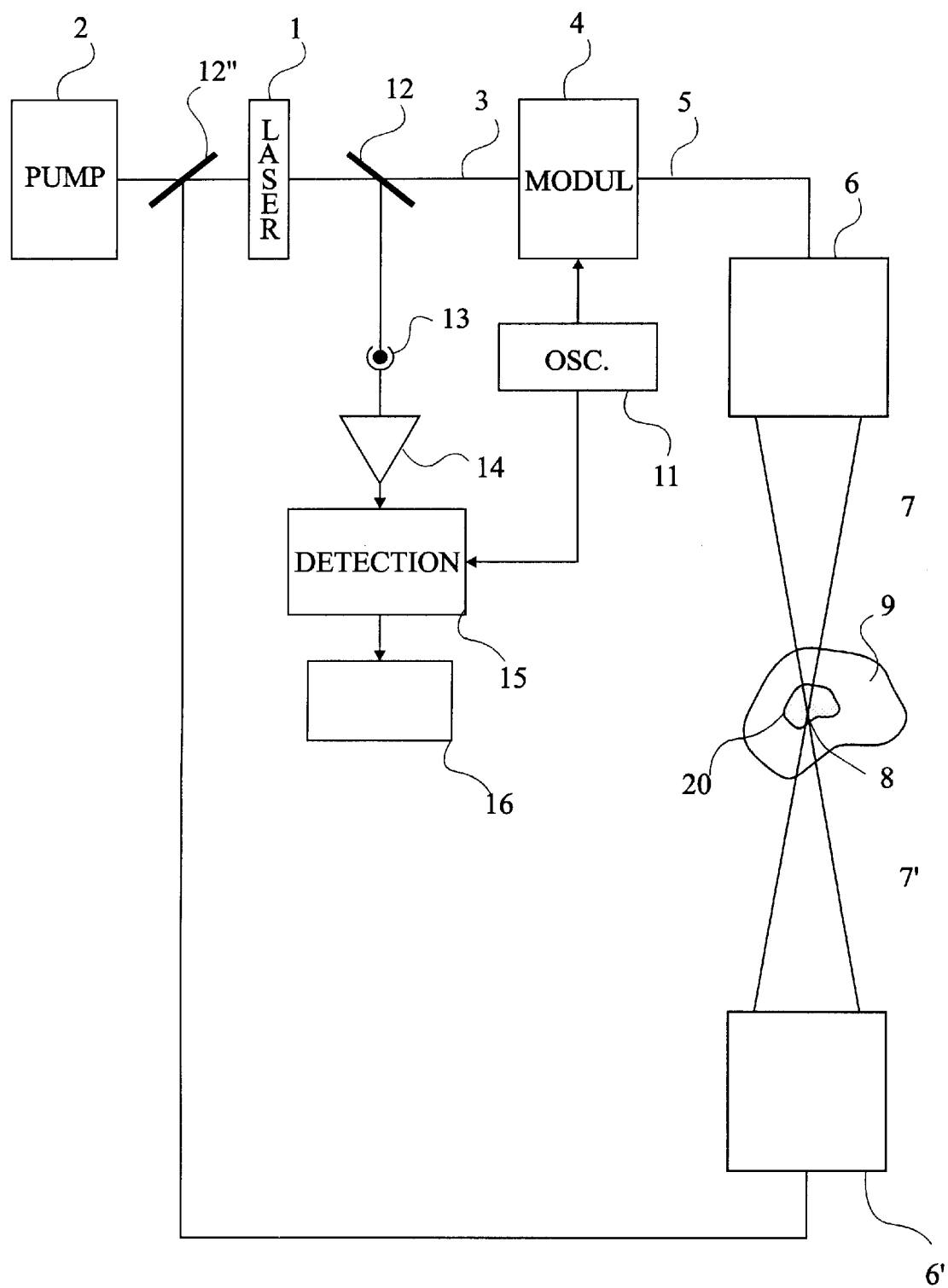
FIG. 3 is a schematic block diagram of a third embodiment of the present invention.

FIGS. 2 and 3 show alternatives of the device of FIG. 1. In these alternatives, same elements are designated by same references.

FIG. 2 shows a system which is very similar to that of FIG. 1 but in which beam splitter 12 (placed between the laser and modulator 4 in FIG. 1) is replaced with a beam splitter 12' placed on the other side of the laser, for example between the laser and the optical pump in FIG. 2.

FIG. 3 shows another alternative of the system in which the light back-scattering or reflection system is replaced with a transmission system. The light is sent to the studied medium in the same way as previously discussed by a laser 1, a modulator 4, and a lens 6. Light 7' having crossed the medium is received by a lens 6' that provides an image of the focus point and this light is reinjected into the laser by a beam splitter 12".

Sensor Use

The use of the sensor according to the present invention in the back-scattering or reflection mode such as illustrated in relation with FIGS. 1 and 2 will more specifically be described hereafter. Those skilled in the art can easily adapt these explanations to the transmission operating mode such as illustrated in FIG. 3.

If, for example, it is desired to identify (see FIG. 1) a body 20 having with a diffusing medium 9 an interface with a diffusion/reflection coefficient distinct from that of the diffusing medium, lens 6 is set in distance until a peak of reemitted light is observed, indicating that the interface level has been reached. Various shifting means may be provided along directions x, y, and z and in rotation to provide an image of body 20.

Interfaces or inhomogeneities of a medium may also exhibit particularly marked diffusion/reflection variations at certain wavelengths. A variable-wavelength laser 1 may then be provided and the laser setting may be modified to adapt to the wavelength at the level of which the detection is likely to be the highest. This can in particular be used to detect the presence or the absence of a gas in a medium, for example to form a gas leak sensor.

Of course, the present invention is likely to have various alterations and modifications which will occur to those skilled in the art. In particular, the radiofrequency generator may provide two frequencies F1 and F2 and the demodulation may be performed on a combination of these two frequencies, for example, F1–F2.

Further, the various optical paths, especially between laser 2 and lens 6, may follow optical fibers and the present invention may be adapted to endoscope-type systems.

The detection by selective reinjection with a class B laser may be made multiplex by for example using:

several units connected by optical fibers to optical system 6;

a one- or two-dimensional array of class B lasers shifted by the same optical frequencies and a one- or two-dimensional array of photodetectors;

a one- or two-dimensional array of class B lasers shifted by different optical frequencies, and a photodetector followed by a demodulator ensuring a demodulation at the various frequencies.

Theoretical Explanation

Although this does not belong to the present invention, various calculations and equations enabling a better understanding of the phenomenon implemented by the present invention will be given hereafter as an indication. However, this must not be considered as limiting the present invention.

The principle of the method can be understood in terms of laser gain modulation, which modulation is induced by the reinjecting of a frequency-shifted portion of the laser. This gain modulation results from an interaction between oscillating electric field $E_L$ in the laser cavity and reinjected electric field $E_{L,S}$ shifted by a frequency F.

The most general equations to describe the system dynamics are the injected laser equations (see for example A. E. Siegmann, *Lasers*, ed. University Science Books, 1986).

In the case where the laser is a class B laser, the following equation system is obtained:

$$\frac{dN}{dt} = \frac{N_0 - N}{T_1} - B|E_L|^2 N \tag{1}$$

$$\frac{dE_L}{dt} = \frac{BE_L N}{2} - \frac{E_L}{2T} + \frac{1}{T} E_{L,S} \cos(\Psi_L(t) + \Phi_{L,S}(t)) \tag{2}$$

$$\frac{d\Psi_L}{dt} = \omega_L - \omega_{L,S} - \frac{1}{T}\frac{E_{L,S}}{E_L} \sin(\Psi_L(t) + \Phi_{L,S}(t)) \tag{3}$$

where:

N is the population inversion, $T_1$ is the lifetime of the population inversion, $\Psi_L$ is the phase difference between electric fields $E_L$ and $E_{L,S}$, $\Phi_{L,S}$ is the phase fluctuation of the reinjected light in the cavity, $\omega_L$ is the optical frequency of electric field $E_L$ in the cavity, $\omega_{L,S}$ is the optical frequency of reinjected electric field $E_{L,S}$ in the laser cavity, T is the photon lifetime in the cavity, B is the Einstein coefficient.

Order of Magnitude

In the system according to the present invention, in which the reinjection is low and ratio $m_S = 2E_{L,S}/E_L$ is small, the second term of equation (3) can be neglected. In the case of a laser injected by an external source, this amounts to saying that the laser is outside the bonding area defined by:

$$\frac{\Delta\omega}{2\pi} = \frac{1}{T}\frac{E_{L,S}}{E_L}.$$

Integrating equation (3) provides:

$$\Psi(t) = (\omega_L - \omega_{L,S})t + C = 2\pi F t + C$$

where C is an integration constant.

The electric field reinjected in the laser cavity is obtained by writing:

$$E_{L,S}(t) = \frac{m_S}{2} E_L(t-t_d)$$

where $t_d$ is the time taken by the wave emitted and reinjected in the laser to leave and return. Time $t_d$ being short as compared to the inverse of frequency F, this pure delay is neglected. In these conditions, with a light intensity $I_L=|E_L|^2$ in the laser cavity and using the following reduced variables:

$\tau=t/T_1$; $n=BTN$ $\alpha=N_0BT$; $s=BT_1I$; $\gamma=T_1/T$,
the following equation system is obtained:

$$\frac{ds}{d\tau} = \gamma(n-1)s + \gamma s m_s \cos(2\pi Ft + \Phi_{L,S}(t)) \quad (4)$$

$$\frac{dn}{d\tau} = \alpha - n - ns \quad (5)$$

s describes the laser intensity and n the population inversion. This system effectively describes a laser for which the gain or losses are modulated.

In the absence of a reinjection, the stationary values of the intensity and the population inversion respectively are:
$s_{st}=\alpha-1$ and $n_{st}=1$ For a very low reinjection ($m_s \ll 1$), equations (4) and (5) become:

$$\frac{d\Delta n}{dt} = -\alpha \Delta n - \Delta s$$

$$\frac{d\Delta s}{dt} = \gamma s_{st}\Delta n + \gamma m_s s_{st}\cos(2\pi Ft + \Phi_{L,S}(t))$$

where $\Delta n$ and $\Delta s$ respectively are the variation of the population inversion and of the light intensity in the vicinity of stationary values $n_{st}$ and $s_{st}$.

By suppressing the population inversion, the equation describing the modulation of the light intensity emitted by the laser is obtained:

$$\frac{d^2\Delta s}{dt^2} + \alpha d\Delta\frac{s}{dt} + \gamma(\alpha-1)\Delta s = \gamma(\alpha-1)m_s[\alpha\cos(2\pi Ft + \Phi_{L,S}) - 2\pi F\sin(2\pi Ft + \Phi_{L,S})]$$

Solving this equation provides the expression of the modulation amplitude of the light intensity emitted by the reinjected laser according to frequency shift F.

$$|\Delta s(\Omega)| = \frac{\sqrt{\Omega^2 + \alpha^2}}{\sqrt{(\omega_0^2 - \Omega^2) + \alpha^2\Omega^2}}\gamma(\alpha-1)m_s$$

with $\Omega=2\pi F$ and $\omega_0^2=\gamma(\alpha-1)$.

This function has a resonance for $$F = \frac{\sqrt{\gamma(\alpha-1)}}{2\pi}.$$

The light modulation rate then transits through a maximm, which is:

$$\frac{|\Delta s(\Omega=\omega_0)|}{s_{st}} = \frac{\sqrt{\omega_0^2 + \alpha^2}}{\alpha\omega_0}\gamma m_s \approx \frac{\gamma}{\alpha}m_s.$$

This modulation signal is on the order of $10^3$ times greater than for the signal obtained by means of a conventional heterodyne detection (without anplification by the laser) in the case where the laser is a laser diode, and of $10^6$ for a solid laser of microlaser type. These very high amplification coefficients ($10^3$ to $10^6$) are the advantage of the system according to the present invention.

We claim:

1. An optical sensor, comprising:
   a class B laser source (1) emitting a beam (3) at a first optical frequency;
   means (4) interacting with the beam (3) to provide a radiation (5) at a modified optical frequency, the shifting between the first frequency and the modified frequency being close to a relaxation frequency of the laser:
   means (6) for irradiating a selected area of a medium to be studied with the radiation at the modified frequency;
   means (6; 6'; 12") for injecting into the laser the light sent back by the selected area; and
   means (9, 14, 15, 16) for detecting the disturbance brought to the laser emission by the reinjected light.

2. The optical sensor of claim 1, further comprising:
   means for scanning the area to be studied.

3. The optical sensor of claim 1, further comprising:
   means for scanning the frequency of the radiation emitted by the laser.

4. The optical sensor of claim 1, wherein the irradiation means (6) are armed of a lens.

5. The optical sensor of claim 1, wherein the detection means includes a photodetector (9) followed by a synchronous detection system (15).

6. The optical sensor of claim 1, wherein the means (4) for providing a radiation at a modified optical frequency consist of a medium having an electro-optical or acousto-optical effect excited by an oscillator at a frequency corresponding to the difference between the modified optical frequency and the first optical frequency or one of its submultiples.

* * * * *

UNITED STATES PATENT AND TRADEMARK OFFICE
CERTIFICATE OF CORRECTION

PATENT NO. : 6,476,916 B1 Page 1 of 1
DATED : November 5, 2002
INVENTOR(S) : Lacot et al.

It is certified that error appears in the above-identified patent and that said Letters Patent is hereby corrected as shown below:

<u>Title page,</u>
Item [57], ABSTRACT, should read:
-- The present invention relates to an optical sensor including a class B laser source emitting a beam at a first optical frequency; means interacting with the beam to provide a radiation at a modified optical frequency, the shifting between the first frequency and the modified frequency being close to a relaxation frequency of the laser; means for irradiating a selected area of a medium to be studied with the radiation at the modified frequency; means for injecting into the laser light sent back by the selected area; and means for detecting the disturbance brought to the laser emission by the reinjected light. --

Signed and Sealed this

Third Day of June, 2003

JAMES E. ROGAN
*Director of the United States Patent and Trademark Office*